United States Patent [19]

Meek et al.

[11] Plant 4,584

[45] Jul. 29, 1980

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 20,773

[22] Filed: Mar. 15, 1979

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A chrysanthemum plant known by the cultivar name Lodestar having flat capitulum form; spooned daisy capitulum type; dark yellow ray floret color; diameter across face of capitulum ranging from 70 to 75 mm at maturity; uniform eight week photoperiodic flowering response to short days; short plant height when grown as a pinched spray pot, and spreading branching pattern.

3 Drawing Figures

The present invention comprises a new and distinct cultivar of *Chrysanthemum morifolium,* Ramat., hereinafter referred to by the cultivar name Lodestar.

Lodestar is a product of a planned breeding program which had the objective of creating new chrysanthemum cultivars with spooned daisy capitulum type, with yellow ray floret color, with eight week flowering response, and with the ability to produce commercially acceptable quality in year round pot mum programs. Such traits in combination were not present in previously available commercial cultivars.

Lodestar was originated from a cross made in a controlled breeding program in Barberton, Ohio in 1976. The female parent was #76047021 (unnamed seedling), a yellow spooned daisy originated from a cross between #75081001 (unnamed seedling) and Spice (U.S. Plant Pat. No. 3,777). The male parent of Lodestar was #75176001 (unnamed seedling), a bronze spooned daisy originated from a cross between #73116031 (unnamed seedling) and #73132001 (unnamed seedling).

Lodestar was discovered and selected as one flowering plant within the progeny of the stated cross by Jack M. Meek and William E. Duffett on May 2, 1977 in a controlled environment in Barberton, Ohio.

The first act of asexual reproduction of Lodestar was accomplished when vegetative cuttings were taken from the initial selection in July, 1977 in a controlled environment in Barberton, Ohio, by a technician working under formulations established and supervised by Jack M. Meek and William E. Duffett. Continued asexual reproduction by vegetative cuttings for evaluative tests in flowering and stock programs in conjunction with horticultural examination of selected units initiated Apr. 28, 1978, has demonstrated that the combination of characteristics as herein disclosed for Lodestar is firmly fixed and retained through successive generations of asexual reproduction.

Lodestar has not been observed under all possible environmental conditions. The phenotype may vary significantly with variations in environment such as temperature, light intensity and daylength. The following observations, measurements, and comparisons describe plants grown in Salinas, Calif. under greenhouse conditions which approximate those generally used in commercial practice.

The following traits have been repeatedly observed and are determined to be basic characteristics of Lodestar which in combination distinguish this chrysanthemum as a new and distinct cultivar:

(1) Flat capitulum form.

(2) Spooned daisy capitulum type.

(3) Dark yellow ray floret color.

(4) Yellow-green (immature) to yellow (mature) disc floret color.

(5) Diameter across face of capitulum ranging from 70 to 75 mm at maturity.

(6) Uniform eight week photoperiodic flowering response to short days.

(7) Short plant height (requiring 2–3 long day weeks prior to pinch and short days, and one application 2500 ppm B-9 SP 14 to 21 days after the beginning of short days to attain a flowered plant height of 30 to 45 cm).

(8) Spreading branching pattern.

The accompanying photographic drawings show typical inflorescence and foliage characteristics of Lodestar with colors being as nearly true as possible with illustrations of this type. Sheet 1 is a color photograph of a flowering plant of Lodestar. Sheet 2 is a black and white photograph showing three views of the inflorescence of Lodestar. Sheet 3 is a black and white photograph showing the foliage of Lodestar at three stages of growth.

Of the many commercial cultivars known to the present inventors, the most similar in comparison to Lodestar is Spice, disclosed in U.S. Plant Pat. No. 3,777 to Walter H. Jessel, Jr. and William E. Duffett. Reference is made to attached Chart A which compares certain characteristics of Lodestar to those same characteristics of Spice. General comparisons are as follows;

In comparison to Spice, Lodestar has more spreading branching pattern, smaller diameter across face of capitulum, and shorter plant height. The ray floret color, capitulum form, capitulum type, and flowering response period of Lodestar are similar to those same characteristics of Spice.

In the following description color references are made to A Limit Color Cascade by the Munsell Company, 1972 edition. The color values were determined between 3:30 and 4:00 p.m. on Jan. 22, 1978 under 150 foot-candle light intensity at Salinas, Calif.

CLASSIFICATION

*Botanical.—Chrysanthemum morifolium,* Ramat., cv Lodestar.

*Commercial.*—Pinched spray pot mum.

I. INFLORESCENCE (See Sheets 1 and 2).

A. Capitulum:
*Form.*—Flat.
*Type.*—Spooned daisy.
*Diameter across face.*—70 to 75 mm.

B. Corolla of ray florets:
*Shape.*—Tubular with flare at petal tip.
*Color (abaxial).*—26-4 to 26-5 inside petal tip.
*Color (adaxial).*—26-4.

C. Corolla of disc florets:
*Color.*—19-6 (immature) to 28-7 (mature).

D. Reproductive organs:
*Androecium.*—Present disc florets only; scant to numerous; sparse to no pollen production.
*Gynoecium.*—Present both ray and disc florets.

II. PLANT

A. General appearance:
*Height.*—Short, requiring 2–3 long day weeks prior to pinch and short days, and one application 2500 ppm B-9 14 to 21 days after the beginning of short days to attain a flowered plant height of 30 to 45 cm.
*Branching pattern.*—Spreading.

B. Foliage (see sheet 3):
*Color (abaxial).*—Approximately 21-14.
*Color (adaxial).*—Approximately 21-13 overlaid with white.

*Shape.*—Moderately lobed; slightly serrated.

Chart A

| | Comparison of Lodestar and Spice | | | | | |
|---|---|---|---|---|---|---|
| Cultivar | Ray Floret color | Capitulum Form and Type | Branching Pattern | Diameter Across Face of Capitulum | Plant Height | Flowering Response Period |
| Lodestar | Dark Yellow | Flat spooned daisy | Spreading | 70 to 75 mm. | Short | 8 week |
| Spice | Dark Yellow | Flat spooned daisy | Semi-spreading | 75 to 80 mm. | Medium | 8 week |

Comparisons made of plants grown as pinched spray pots in Salinas, California.

We claim:

A new and distinct cultivar of *Chrysanthemum morifolium,* Ramat., plant as shown and described, known by the cultivar name Lodestar and particularly characterized as to uniqueness by the combined characteristics of flat capitulum form; spooned daisy capitulum type; dark yellow ray floret color; diameter across face of capitulum ranging from 70 to 75 mm at maturity; uniform eight week photoperiodic flowering response to short days; short plant height when grown as a pinched spray pot, and spreading branching pattern.

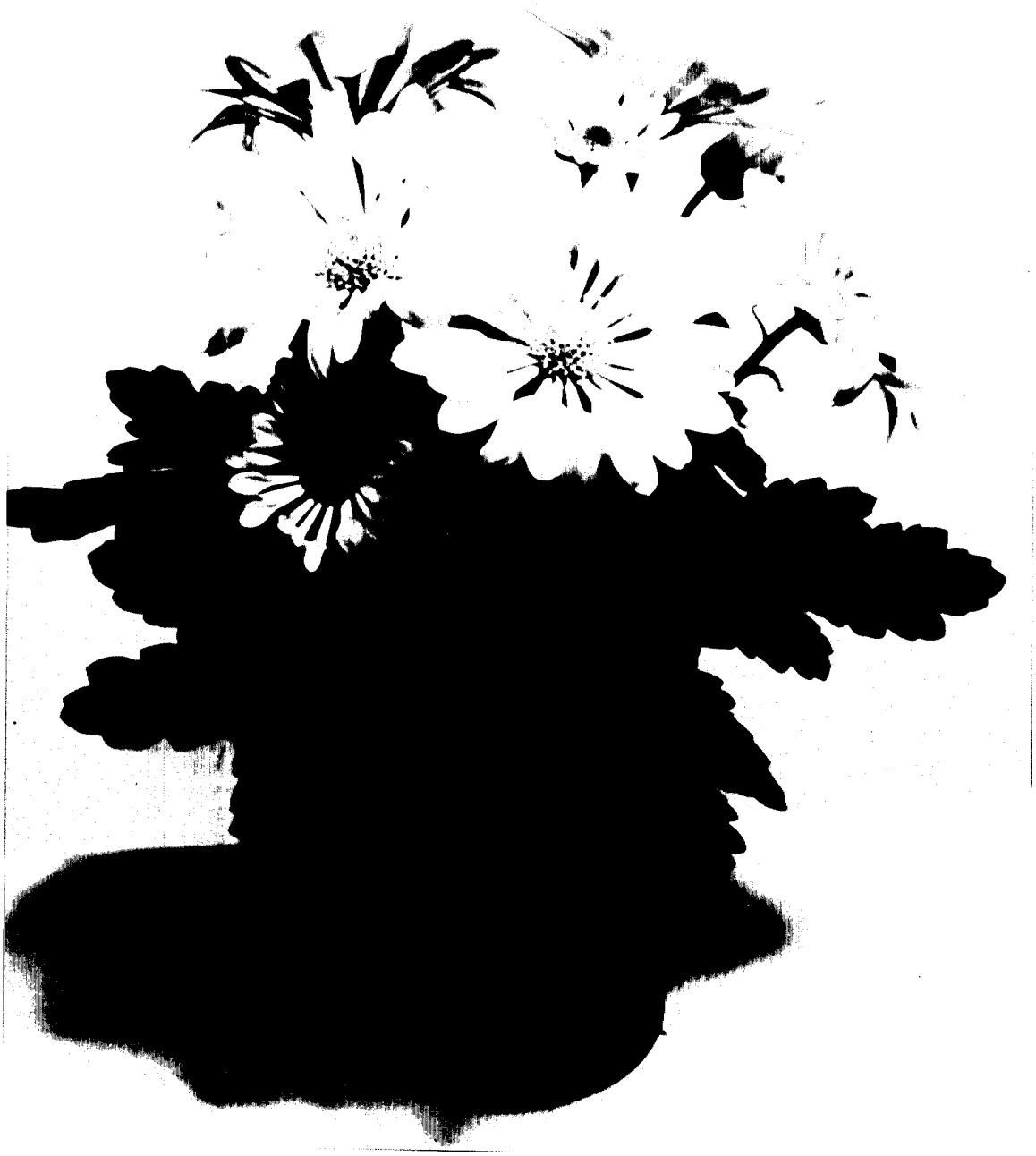

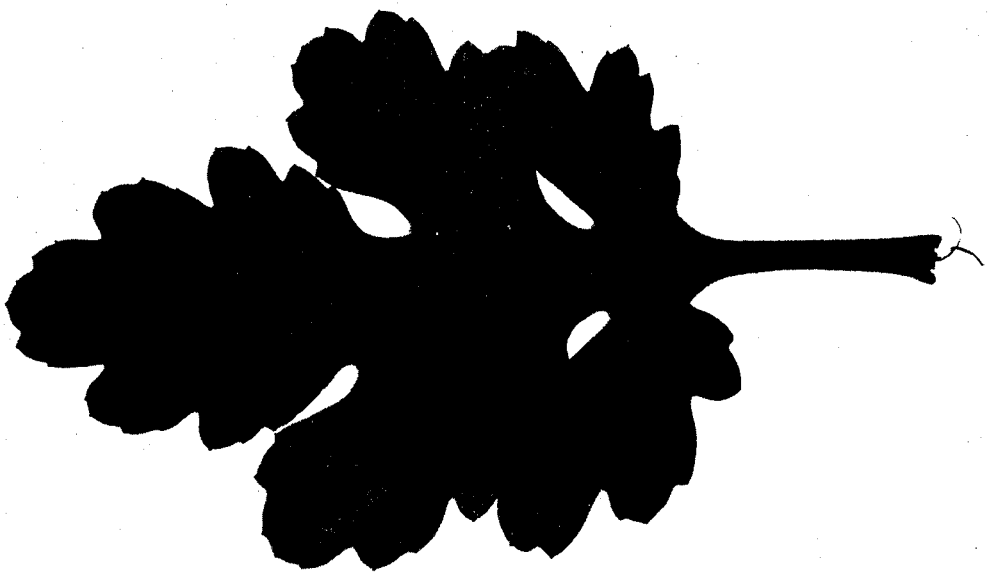
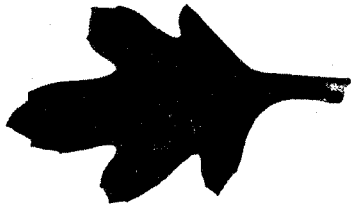
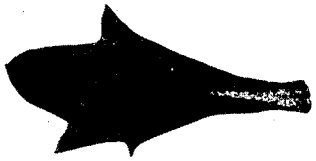

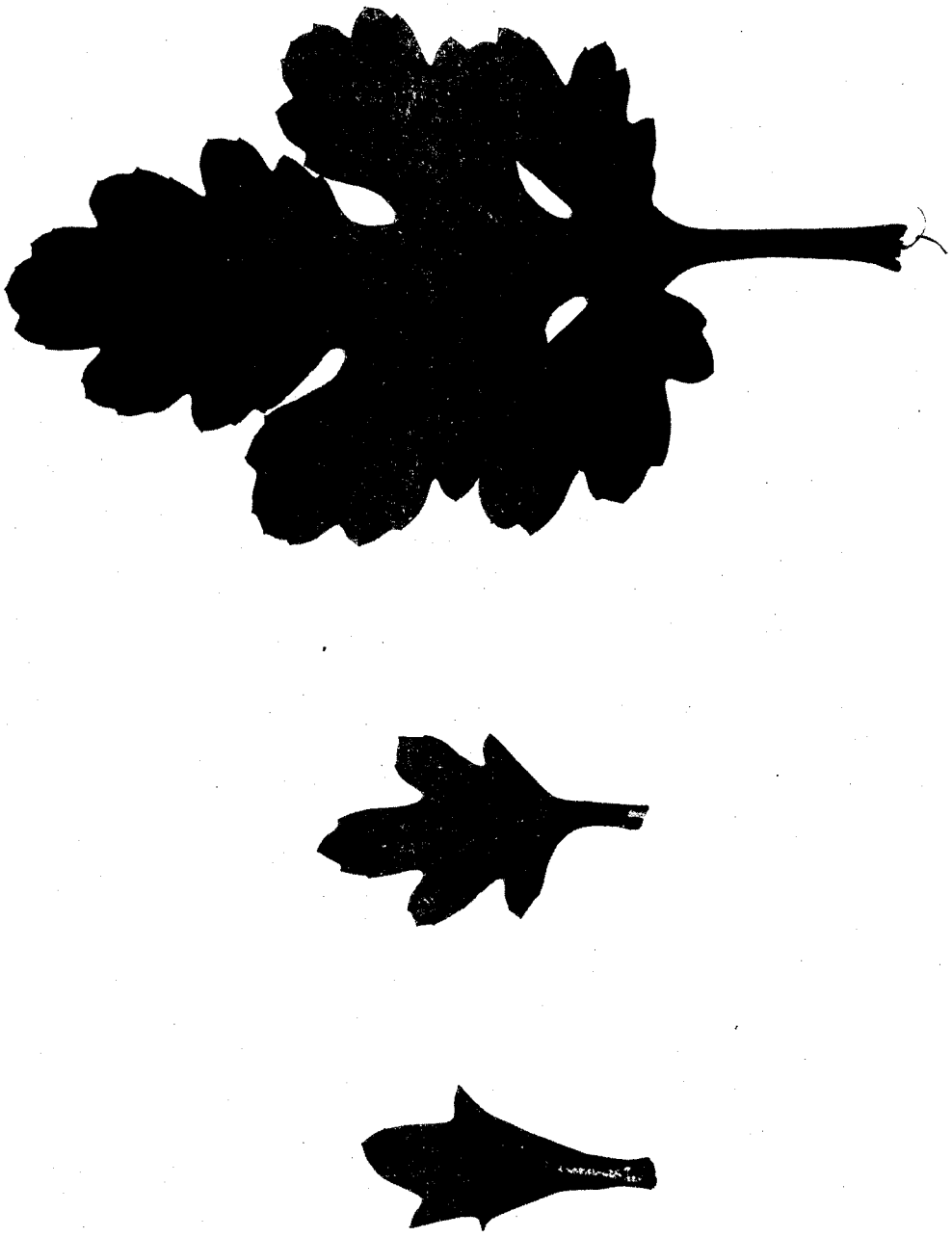

* * * * *